(12) United States Patent
Al-Terki

(10) Patent No.: US 9,295,700 B1
(45) Date of Patent: Mar. 29, 2016

(54) WOUND HEALING COMPOSITION

(71) Applicant: Abdulmohsen Ebrahim Al-Terki, Safat (KW)

(72) Inventor: Abdulmohsen Ebrahim Al-Terki, Safat (KW)

( * ) Notice: Subject to any disclaimer, the term of this patent is extended or adjusted under 35 U.S.C. 154(b) by 0 days.

(21) Appl. No.: 14/944,202

(22) Filed: Nov. 17, 2015

(51) Int. Cl.
*A01N 65/00* (2009.01)
*A61K 35/644* (2015.01)
*A61K 36/88* (2006.01)
*A61L 15/44* (2006.01)
*A61L 15/40* (2006.01)

(52) U.S. Cl.
CPC ............... *A61K 35/644* (2013.01); *A61K 36/88* (2013.01); *A61L 15/40* (2013.01); *A61L 15/44* (2013.01); *A61L 2300/30* (2013.01); *A61L 2300/606* (2013.01)

(58) Field of Classification Search
CPC .................................................... A61K 36/00
USPC ........................................................ 424/725
See application file for complete search history.

(56) References Cited

U.S. PATENT DOCUMENTS 4,382,886 A    5/1983  Sosnowski
6,521,269 B2   2/2003  Tao

FOREIGN PATENT DOCUMENTS

| CN | 103756858 A   | 4/2014 |
| CN | 103919967 A   | 7/2014 |
| KR | 2001-0008260  | 2/2001 |
| RU | 2002108231    | 1/2004 |

OTHER PUBLICATIONS

Gupta et al., "Dragon's Blood: Botany, Chemistry, and Therapeutic Uses," *Journal of Ethnopharmacology*, 2008, 361-380.

*Primary Examiner* — Michael Meller
(74) *Attorney, Agent, or Firm* — Richard C. Litman

(57) ABSTRACT

The wound healing composition is a composition for topical application in or on a wound that is believed to promote hemostasis and tissue growth. The wound healing composition includes a mixture of *Dracaena cinnabari* (dragon's blood), propolis (bee's glue) extract powder, and honey, preferably seder honey. An exemplary wound healing composition includes about 25 gm seder honey, 1.5 gm of 70% propolis extract powder, and about 1 gm *D. cinnabari* powder. The powders are mixed into the viscous honey base, and the composition may be applied directly to the wound. Alternatively, the composition may be applied to sterile gauze, and the wound, particularly an open surgical wound, may be packed with the gauze, or the gauze may be applied as a wound dressing.

4 Claims, No Drawings

WOUND HEALING COMPOSITION

BACKGROUND OF THE INVENTION

1. Field of the Invention

The present invention relates to herbal compositions, and particularly to a wound healing composition.

2. Description of the Related Art

Bleeding, and in some cases abnormal or uncontrolled bleeding, can result from surgical procedures designed to treat patients with diseases and disorders of the ear, nose, and throat and related structures of the head and neck, as well as from a variety of other types of surgeries anywhere else in the body. Bleeding can be one of the biggest complications, not only when performing the surgical procedure as the bleeding can obscure the surgical area, but also when completing a procedure, as the excess blood can hinder a doctor when closing a surgical wound, such as while an incision is being closed.

Typically, doctors use suction devices to eliminate any excess blood and to clear the surgical area on the patient's body while a doctor is performing surgery. Sutures are used to immediately close the wound and prevent further bleeding. However, while stiches and other types of sutures can provide immediate benefits, not all bleeders are accessible, and many times sutures can also result in scars and other types of unseemly marks that can remain on the patient's skin permanently for all to see, which can be a source of embarrassment for many individuals. Although band-aids are also used to cover scrapes and other cuts and bruises, band-aids typically do not sterilize the area where the person cut him or herself, which can lead to infection and further complications.

Thus, a wound healing composition solving the aforementioned problems is desired.

SUMMARY OF THE INVENTION

The wound healing composition is a composition for topical application in or on a wound that is believed to promote hemostasis and tissue growth. The wound healing composition includes a mixture of *Dracaena cinnabari* (dragon's blood), propolis (bee's glue) extract powder, and honey, preferably seder honey. An exemplary wound healing composition includes about 25 gm seder honey, 1.5 gm of 70% propolis extract powder, and about 1 gm *D. cinnabari* powder. The powders are mixed into the viscous honey base, and the composition may be applied directly to the wound. Alternatively, the composition may be applied to sterile gauze, and the wound, particularly an open surgical wound, may be packed with the gauze, or the gauze may be applied as a wound dressing.

These and other features of the present invention will become readily apparent upon further review of the following specification.

DETAILED DESCRIPTION OF THE PREFERRED EMBODIMENTS

The wound healing composition is a composition for topical application in or on a wound that is believed to promote hemostasis and tissue growth. The wound healing composition includes a mixture of *Dracaena cinnabari* (dragon's blood), propolis (bee's glue) extract powder, and honey, preferably seder honey. An exemplary wound healing composition includes about 25 gm seder honey, 1.5 gm of 70% propolis extract powder, and about 1 gm *D. cinnabari* powder. The powders are mixed into the viscous honey base, and the composition may be applied directly to the wound. Alternatively, the composition may be applied to sterile gauze, and the wound, particularly an open surgical wound, may be packed with the gauze, or the gauze may be applied as a wound dressing.

The *Dracaena cinnabari* used in the present composition is a crimson resin obtained from *D. cinnabari*, the Socotra dragon tree or dragon blood tree, which is native to the Socotra archipelago in the Indian Ocean. It is one of several plant species that produce the red sap or resin popularly thought to resemble dragon's blood. Dragon's blood has historically been used as an astringent and for wound healing in traditional medicine.

Propolis is a resin or sap from trees and flowers that is collected by honey bees and used as a kind of glue to seal openings or holes in their hives. Propolis contains antioxidants, and some research studies have suggested that propolis exhibits antimicrobial properties, although such findings have not been confirmed by clinical studies. Propolis has been extracted and marketed in both liquid and powder form for both cosmetic and alternative medicine use.

Honey serves as a base for the wound healing composition, and also contains antioxidants believed to exhibit antibacterial and antimicrobial properties. The *Dracaena Cinnabari* powder and the 70% propolis extract powder are mechanically mixed with the honey to form a homogenous mixture.

By way of operation, in order to make the wound healing composition, a user can mix approximately 1 gram of *Dracaena Cinnabari* powder together with approximately 1.5 grams of 70% propolis extract powder so as to form a homogenized mixture. Subsequently, the user can mix the homogenous mixture of powders and 25 grams of seder honey to form the wound healing composition. Once the wound healing composition is completed, the wound healing composition can either be applied directly to the wound on the patient's skin or can be mixed with a sterile gauze which can them be positioned in or on the wound. It is believed that the composition promotes hemostasis while providing an antibacterial and antimicrobial dressing that promotes tissue growth, accelerating wound healing.

It is to be understood that the present invention is not limited to the embodiments described above, but encompasses any and all embodiments within the scope of the following claims.

I claim:

1. A sterile gauze consisting essentially of: a sterile gauze and a wound dressing composition, wherein the wound dressing composition consists essentially of honey, propolis extract and *Dracaena cinnabari* extract.

2. The sterile gauze of claim 1, wherein the honey is seder honey.

3. The sterile gauze of claim 1, wherein the propolis extract is a powder which is 70% propolis extract.

4. The sterile gauze of claim 1, wherein the composition is about 25 grams honey, about 1.5 grams 70% propolis extract powder; and about 1 gram *Dracaena cinnabari* powder.

* * * * *